US009463176B2

(12) United States Patent
Hageman

(10) Patent No.: US 9,463,176 B2
(45) Date of Patent: Oct. 11, 2016

(54) COMPOSITION FOR IMPROVING MEMBRANE COMPOSITION AND FUNCTIONING OF CELLS

(75) Inventor: Robert J. J. Hageman, Wageningen (NL)

(73) Assignee: N.V. Nutricia (NL)

( * ) Notice: Subject to any disclaimer, the term of this patent is extended or adjusted under 35 U.S.C. 154(b) by 750 days.

(21) Appl. No.: 13/294,587

(22) Filed: Nov. 11, 2011

(65) Prior Publication Data

US 2012/0064127 A1   Mar. 15, 2012

Related U.S. Application Data

(63) Continuation of application No. 12/142,972, filed on Jun. 20, 2008, now Pat. No. 8,076,282, which is a continuation of application No. PCT/NL2006/000658, filed on Dec. 22, 2006.

(30) Foreign Application Priority Data

Dec. 23, 2005   (EP) .................................... 05077972

(51) Int. Cl.
| A61K 33/24 | (2006.01) |
| A61K 31/202 | (2006.01) |
| A23L 1/29 | (2006.01) |
| A23L 1/30 | (2006.01) |
| A23L 1/302 | (2006.01) |
| A23L 1/304 | (2006.01) |
| A23L 1/305 | (2006.01) |
| A61K 31/185 | (2006.01) |
| A61K 31/198 | (2006.01) |
| A61K 31/20 | (2006.01) |
| A61K 33/32 | (2006.01) |
| A61K 35/20 | (2006.01) |
| A61K 45/06 | (2006.01) |

(52) U.S. Cl.
CPC .............. *A61K 31/202* (2013.01); *A23L 1/296* (2013.01); *A23L 1/302* (2013.01); *A23L 1/304* (2013.01); *A23L 1/305* (2013.01); *A23L 1/3008* (2013.01); *A61K 31/185* (2013.01); *A61K 31/198* (2013.01); *A61K 31/20* (2013.01); *A61K 33/24* (2013.01); *A61K 33/32* (2013.01); *A61K 35/20* (2013.01); *A61K 45/06* (2013.01); *A23V 2002/00* (2013.01)

(58) Field of Classification Search
None
See application file for complete search history.

(56) References Cited

U.S. PATENT DOCUMENTS

| 4,544,559 A | 10/1985 | Gil et al. |
| 4,758,553 A | 7/1988 | Ogoshi |
| 5,223,285 A | 6/1993 | DeMichele et al. |
| 5,231,085 A | 7/1993 | Alexander et al. |
| 5,895,652 A * | 4/1999 | Giampapa ................ 424/195.17 |
| 6,187,761 B1 | 2/2001 | Bijl |
| 6,194,379 B1 | 2/2001 | McEwen et al. |
| 6,339,085 B1 | 1/2002 | Haque |
| 6,391,362 B1 | 5/2002 | Gorewit |
| 6,548,519 B1 | 4/2003 | Haque |
| 6,586,614 B2 | 7/2003 | Cowan |
| 6,753,350 B1 | 6/2004 | Hansen et al. |
| 6,824,809 B2 | 11/2004 | Goudedranche et al. |
| 7,090,879 B2 | 8/2006 | Albrecht et al. |
| 2002/0004527 A1 | 1/2002 | Auestad et al. |
| 2000/5000977 | 1/2005 | Kiliaan et al. |
| 2005/0176676 A1 | 8/2005 | Watkins et al. |
| 2005/0203053 A1 | 9/2005 | Wurtman et al. |
| 2006/0280776 A1 | 12/2006 | Koide |
| 2008/0292724 A1 | 11/2008 | Hageman et al. |
| 2008/0317868 A1 | 12/2008 | Hageman et al. |
| 2009/0022813 A1 | 1/2009 | Hageman |

FOREIGN PATENT DOCUMENTS

| AU | 2000022638 A1 | 6/2000 |
| CN | 1155982 A | 8/1997 |
| CN | 1239644 A | 12/1999 |
| CN | 1436048 A | 8/2003 |
| EP | 0231904 A2 | 8/1987 |

(Continued)

OTHER PUBLICATIONS

Office Action issued for corresponding Chinese Patent Application No. 200680052701.3, dated Mar. 3, 2014.
English Translation of Office Action issued for corresponding Chinese Patent Application No. 200680052701.3, dated Mar. 3, 2014.

(Continued)

*Primary Examiner* — Anand Desai
(74) *Attorney, Agent, or Firm* — Banner & Witcoff, Ltd.

(57) ABSTRACT

It has now been found that after administration to a diseased person or person that is at risk for developing such disease of a neutraceutical or pharmaceutical composition that comprises a) a lipid fraction comprising at least one of docosahexaenoic acid (DHA), docosapentaenoic acid (DPA) and eicosapentaenoic acid (EPA);

b) a protein fraction comprising proteinaceous material from non-human origin which provide at least cysteine and/or taurine; and c) a mineral fraction comprising at least one of manganese and molybdenum, the health of these persons improves. Membrane function of several types of mammalian cells improves, which allows efficient treatment of immune related disorders, such as allergy, autoimmune diseases, cancer, cognitive dysfunction and other diseases of the nervous system, neuropathies, such as diabetic neuropathies and neuropathic pains, neuronal damage during insulin resistance, and gut diseases and support of the development of gut and lung function during growth or recovery.

20 Claims, 1 Drawing Sheet

(56) References Cited

FOREIGN PATENT DOCUMENTS

| | | |
|---|---|---|
| EP | 0302481 A2 | 8/1988 |
| EP | 0311091 A1 | 4/1989 |
| EP | 0367724 A1 | 10/1989 |
| EP | 0484266 A2 | 10/1991 |
| EP | 0891719 A1 | 1/1999 |
| EP | 0951842 A2 | 4/1999 |
| EP | 1279400 A1 | 7/2000 |
| EP | 1041896 A2 | 10/2000 |
| EP | 1426053 A1 | 12/2002 |
| EP | 1714660 A1 | 4/2005 |
| EP | 1665940 A1 | 6/2006 |
| WO | 88/08259 A1 | 11/1988 |
| WO | 94/27628 A1 | 12/1994 |
| WO | 00/06174 A1 | 2/2000 |
| WO | 01/78530 A2 | 10/2001 |
| WO | 02/087593 A1 | 11/2002 |
| WO | 02094035 A1 | 11/2002 |
| WO | 03/037320 A1 | 5/2003 |
| WO | 2004/028529 A1 | 4/2004 |
| WO | 2004/112509 A2 | 12/2004 |
| WO | 2005/023021 A1 | 3/2005 |
| WO | 2005/027663 A2 | 3/2005 |
| WO | 2005/051091 A1 | 6/2005 |
| WO | 2005/060954 A1 | 7/2005 |
| WO | 2005063050 A1 | 7/2005 |
| WO | 2006009437 A2 | 1/2006 |

OTHER PUBLICATIONS

Office Action issued for corresponding U.S. Appl. No. 13/933,172 dated May 6, 2014.
Bougle, D. et al. Molybdenum in the Premature Infant. Biol Neonate 1991; 59:201-203.
"Definition of Nutraceutical", Nutraceutical definition—Medical Dictionary Definitions of Popular Terms Defined on MedTerms, May 27, 2014, p. No. 1.
"Definition of Nutraceutical", Nutraceutical—Medical Definition and More from Merriam-Webster, May 27, 2014, p. No. 1.
Communication issued for corresponding European Patent Application No. 06835683.1, dated Jul. 21, 2014.
Moore, Patricia M. et al, "Neurology of the vasculitides and connective tissue diseases", Neurology and Medicine, J. Neurol Neurosurg Psychiatry, 1998, pp. 10-22, vol. 65.
Brown, et al., "Structure and Function of Sphingolipid-and Cholesterol-rich Membrane Rafts," The Journal of Biological Chemistry, vol. 275, No. 23, Jun. 9, 2000, 17221-17224.
Hashimoto, et al., "Chronic Administration of Docosahexaenoic Acid Ameliorates the Impairment of Spatial Cognition Learning Ability in Amyloid β-Infused Rats," J. Nutr., 135: 549-555, 2005.
Lehner, et al., "Dosage de la graisse dans les farines, en particulier celles contenant du lait, d'après ne modification de la méthode Roese-Gottlieb" ("Proportions of fats in flour, particularly those containing milk after modification by the Roese-Gottlieb method"), Mitt. Lebensmitteluntersuchung Hyg., 45:183-185 (1954) (in French with summary in English).
Ma, et al., "n-3 PUFA and Membrane Microdomains: A New Frontier in Bioactive Lipid Research," Journal of Nutritional Biochemistry 15 (2004) 700-706.
Nettleton, et al., "n-3 Long-Chain Polyunsaturated Fatty Acids in Type 2 Diabetes: A Review," Journal of the American Dietetic Association, 2005, 105:428-440.
Profita, et al,. "Muscarinic Receptors, Leukotriene B4 Production and Neutrophilic Inflammation in COPD Patients," Allergy 2005, 60: 1361-1369.
Crawford, Michael A., "The Role of Essential Fatty Acids in Neural Development: Implications for Perinatal Nutrition," Am. J. Clin. Nutr., 1993, pp. 703S-710S, vol. 57 (suppl), American Society for Clinical Nutrition.
Formai, Francesco, et al.,"Is there a Role for Uridine and Pyrimidine Nucleosides in the Treatment of Vascular Dementia?" Functional Neurology, May 8, 2002, pp. 93-99, vol. 17, No. 2.
Langsjoen, Peter H., et al.,"Potential Role of Concomitant Coenzyme Q10 with Statins for Patients with Hyperlipidemia," Current Topics in Nutraceutical Research, May 10, 2005, pp. 149-158, vol. 3, No. 3, New Century Health Publishers, LLC.
Lukiw, Walter J., et al.,"A Role for Docosahexaenoic Acid-Derived Neuroprotectin D1 in Neural Cell Survival and Alzheimer Disease," The Journal of Clinical Investigation, Oct. 2005, pp. 2774-2783, vol. 115, No. 10.
Pooler, A. M., et al.,"Uridine Enhances Neurite Outgrowth in Nerve Growth Factor-Differentiated Pheochromocytoma Cells," Neuroscience, 2005, pp. 207-214, vol. 134, Elsevier Ltd.
Wang, Lei, et al.,"Dietary Uridine-5'-Monophosphate Supplementation Increases Potassium-Evoked Dopamine Release and Promotes Neurite Outgrowth in Aged Rats," Journal of Molecular Neuroscience, 2005, pp. 137-145, vol. 27, Humana Press Inc.
Office Action issued in corresponding Chinese Patent Application No. 200680052701.3, dated Oct. 9, 2014.
English Translation of Office Action issued in corresponding Chinese Patent Application No. 200680052701.3, dated Oct. 9, 2014.
Office Action issued for corresponding European Patent Application No. 06835683.1, dated Nov. 9, 2015.
European Search Report issued from corresponding 11157253.3, dated Nov. 10, 2015.
Souci et al.; "Cow's Milk"; Food Composition and Nutrition Tables; Jan. 1, 2008, pp. 1-17.
Hebeisen et al.; "Increased concentrations of omega-3 fatty acids in milk and platelet rich plasma of grass-fed cows"; International Journal for Vitamin and Nutrition Research; vol. 63, No. 3, 1993, pp. 229-233.
Deeth H.C.; "The role of phospholipids in the stability of milk fat globules"; Australian Journal of Dairy Technology; vol. 52, vol. 1, 1997, pp. 44-46.
Third Party Observation from corresponding 11157894.4, dated Jul. 6, 2015.
Janas et al.; "The Nucleotide Profile of Human Milk"; pediatr. Res. 16, pp. 659-662 (1982).
Office Action issued for corresponding U.S. Appl. No. 13/933,172, dated Aug. 6, 2015.
Molybdenum in premature infants (Biol Neonate 1991, 59:201-203).
Hambidge et al (Uppoer limits of zinc, copper and manganese in infant formulas, J. Nutr. 1991: 1861-1864, 1989).
Third Party Submission issued in corresponding European Application No. 1157540.3, dated Jan. 15, 2016.
Nealmcb, et al., "Neoplasm",<https://en.wikipedia.org/wiki/Neoplasm?oldid=69182280>.

\* cited by examiner

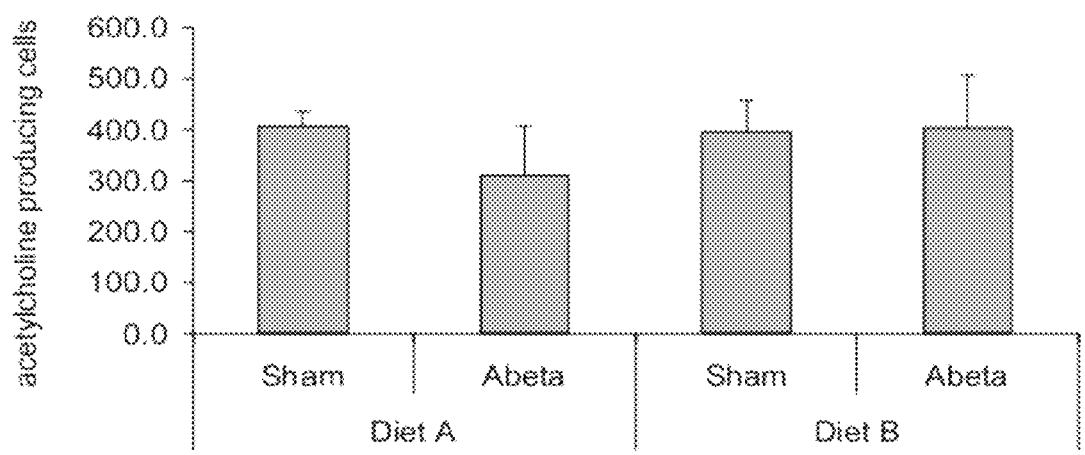
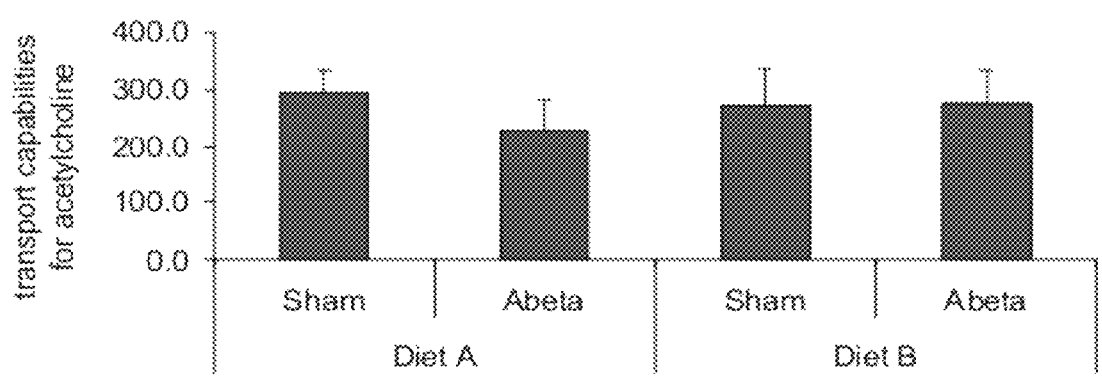

COMPOSITION FOR IMPROVING MEMBRANE COMPOSITION AND FUNCTIONING OF CELLS

RELATED APPLICATION DATA

This application is a continuation of U.S. patent application Ser. No. 12/142,972, filed Jun. 20, 2008 which is a continuation of PCT Application No. PCT/NL2006/000658, filed Dec. 22, 2006 which claims the benefit of the filing date of European Application No. EP 05077972.7, filed Dec. 23, 2005, each of which are hereby incorporated by reference in their entireties.

FIELD

The invention relates to nutraceutical and pharmaceutical compositions, more in particular compositions that can improve membrane composition and functioning of cells and through this the general cell functioning.

BACKGROUND

Membranes in living cells are known to have many important functions. The plasma membrane serves as a barrier to extra-cellular components (e.g. chemical compounds, antigens and cells); membranes (intra cellular as well as the plasma membrane) regulate the transport of components from the exterior to the interior of cells or organelles and vice versa. Membranes form a matrix for many endogenous reactions, for example many enzyme controlled reactions that are important for the biosynthesis, metabolism or catabolism of compounds. Membranes are also important for recognition and modulation of signals from the outside world and therefore contribute to a proper response of the organism. Interaction with the outside world includes the interaction of host cells with foreign cells or parts thereof like antigens/allergens, interaction of host cells with signal molecules like insulin, chemokines, cytokines and hormones and interaction of host cells with each other, such as the interactions between nerve cells, in particular those within the central nerve system (brain and in the spinal chord).

In the art many papers reveal particular aspects of the way living cells interact with extra-cellular signals. Phosphorylation of target proteins in the membrane, as may occur after binding of a receptor with an extra cellular ligand molecule, appears important for type and magnitude of signal transduction. Equally important is the assembly of signaling molecule complexes with specific intracellular or membrane-bound proteins. These proteins, e.g. regulatory or scaffold proteins, may comprise one or more specific domains such as the SH2, the SH3, the PTB, and the PTZ and WW domain types (see G. Cesarini et al. (eds.): *Modular Protein Domains*. Wiley VCH Verlag, 2004). The reaction of the cell to an outside signal also depends on the nature of the membrane. In particular the presence of some phosphatidylinositol (PI)-related compounds appear to be important for the function effected by proteins that possess pleckstrin homology (PH) domains, e.g. protein kinase C (PKC).

The way that a living cell reacts to an extracellular signal can vary widely and includes specific activation of phospholipid metabolism, specific cell adhesion behavior, a change in GTP-ase activity, localization of protein kinase activity, e.g. that of PKC, expression of specific transcription factors, regulation of the sensitivity of insulin receptor, and the spatial arrangement or activity of receptors and of ion channels.

Interaction between nerve cells (neurons) requires activation of ion channels, including the Na+, K+ and Ca2+ channels. In addition the regulation of numbers of receptors, also in relation to the different types of receptors, is important for proper cognitive, emotional and sensorimotoric (like e.g. hearing, smelling, feeling and tasting) functions. Such regulation is also mediated by neuregulin (Nrg-1) and postsynaptic density protein (PSD-95), whose functions appear to be dependent on membrane composition. In the end the signal transduction will result in the activation of a variety of specific genes, which together regulate consciousness, behavior and cognitive and intellectual capabilities.

Cell membranes comprise many types of chemical components, like phospholipids, cholesterol, glycolipids, sphingolipids, sulfatides, cerebrosides, gangliosides, proteins, including glycoproteins, peptides, ions, vitamins, and many other components apart from water. Typically these components are not evenly distributed over the membrane. Polar and non-polar areas can be identified. In particular to the so-called "rafts," the often small non-polar areas in a plasma membrane, specific functions have been allocated (Brown, D. A., London, E., (2000) *J. Biol. Chem.* 275:17221-17224).

Membrane composition is subject to many changes over time due to physical and/or enzymatic processes. Membrane-like structures also form a large part of the Golgi apparatus and the endoplasmatic reticulum (ER) and their structure determines their potential function and properties.

Several methods have been described to influence the interaction between nerve cells and to improve cognitive function.

US 2005/0009779 discloses a method to increase membrane fluidity and to improve receptor function in this way. It was claimed that saturated fatty acids and cholesterol stiffen the membrane and that the combination of long chain polyunsaturated fatty acids together with certain components that improve methionine metabolism can make cell membranes function in a better way. The document is e.g. silent about the importance of the presence of polar membrane constituents other than phospholipids and about the role of food constituents like manganese, molybdenum, taurine, cysteine, sulfate, water and the nature of the carbohydrate fraction in suitable nutritional products for improvement of membrane function.

US 2005/0203053 discloses that neurological function could be improved by enhancing the biosynthesis of phospholipids in the brain. This was achieved by consuming a uridine source, a source of choline and optionally a fatty acid. It was claimed that synaptic transmission was improved; the number of neurites was increased as well as the sensitivity of the P2Y receptor. Similar effects for these food components have been disclosed in US 2005/0176676.

WO 2004/028529 discloses a specific phospholipid comprising arachidonic acid, optionally in combination with medium chain triglycerides or a source of docosahexaenoic acid for improving cognitive function.

WO 2005/051091 discloses a specific blend of glycerophospholipids in combination with sphingomyelin and/or cholesterol, which blend resembles that of human breast milk and is present as a fat globule for use in the manufacture of infant formulae. The blend is claimed to be beneficial for the development of cognitive and vision functions of the fetus, infants and children.

Specific lipid blends have been proposed for treatment of diseases or modifying functioning of an organism.

In EP 1279400 an isotonic lipid emulsion is disclosed which comprises 60-95 wt % MCT and 5-40 wt % fish oil and which comprises no vegetable oils. This lipid blend is claimed to rapidly modify cell membranes of organs and tissues, and to be useful in the treatment of a wide range of diseases.

EP 0311091 discloses a specific lipid blend for parenteral use, which comprises MCT, ω-3 and ω-6 fatty acids, a phospholipid fraction and vitamin E. Such lipid blend is claimed to be useful for patients that suffer from surgery, multiple traumata, burns, infections, lung failure and chronic inflammatory diseases. The product as disclosed does not comprise intact proteins or peptides and is not suitable for complete nutrition.

EP 0484266 discloses nutritional products that comprise DHA and EPA, from about 24 to about 82 mg phospholipids per liter product and a nucleotide mixture, which is claimed to be useful for nourishing infants and for the dietary management of hepatic cirrhosis and diarrhea.

EP 1426053 discloses the use of phospholipids, sphingomyelin, or galactolipid in the preparation of a pharmaceutical composition for parenteral use in inhibiting tumor cell adhesion, inhibition of adhesion of metastasis cells and/or inhibition of tumor metastasis growth. The proposed formulations are unsuitable for complete nutrition by enteral route. No indication is given in what way other food constituents may interfere with the claimed efficacy.

Many papers speculate about the usefulness of eicosapentaenoic acid (EPA) or docosahexaenoic acid (DHA) for treating inflammatory diseases. However, serious difficulties have risen in demonstrating clinical efficacy of the administration of these ω-3 fatty acids. Up to the filing date predominantly in the treatment of arthritis a statistically significant improvement could be observed.

It is an object of the present invention to change the composition of cell membranes (particularly rafts) in several types of cells in a manner that is convenient, in particular by administration of a nicely tasting enteral formulation.

SUMMARY

In an aspect, the invention relates to a lipid fraction comprising at least one of docosahexaenoic acid (DHA), docosapentaenoic acid (DPA) and eicosapentaenoic acid (EPA) and a nucleotide fraction for use as a nutriceutical or pharmaceutical composition for the treatment or prevention of diabetes, obesity and/or insulin resistance.

The invention now provides a nutraceutical or pharmaceutical composition comprising:
a) a lipid fraction comprising at least one of docosahexaenoic acid (DHA), docosapentaenoic acid (DPA) and eicosapentaenoic acid (EPA);
b) a protein fraction comprising proteinaceous material from non-human origin which provide at least cysteine and/or taurine; and optionally
c) a mineral fraction comprising at least one of manganese and molybdenum.

Said composition preferably comprises from about 50 to about 120 kcal per 100 grams. In a first embodiment said composition further comprises a nucleotide fraction, selected from the group consisting of nucleobases like uridine, cytidine, adenine, guanidine, thymidine, their phosphorylated forms, in particular the mono-phosphorylated forms such as uridine monophosphate, but also adenosine and guanosine, nucleotides and nucleosides.

Alternatively, said composition further comprises a digestible carbohydrate fraction, preferably including a source of galactose and/or ribose.

Preferably the lipid fraction is from dairy origin, from eggs or from the endosperm of plant seeds or beans and it preferably comprises fat globules having a size of 0.001-10 µm.

Specific embodiments of the compositions are shown in the detailed description and the examples.

Also provided is the use of a composition according to the invention for improving the function of a mammalian cell, selected from the group of nerve cells, immune cells, stem cells, bone marrow cells and erythrocytes, for improving memory function in a mammal, for stimulating immune function in a mammal, for preventing obesity in a mammal, in autoimmune diseases and the like.

Also part of the invention is the use of said composition for the manufacture of a medicament for the treatment of dementia, such as Alzheimer's disease, neuropathies, depressed immune function, allergy, anemia, obesitas, diabetes, autoimmune diseases, arrhythmias, heart failures, tumors, COPD, bronchitis, arthritis, hepatitis, chronic inflammation, dyslipidaemia and rheumatoid diseases.

BRIEF DESCRIPTION OF THE DRAWINGS

FIG. 1 demonstrates the significant improvement of biosynthesis and transport of acetylcholine when feeding the product according the invention to a rat, which is injected with Aβ.

DETAILED DESCRIPTION OF CERTAIN PREFERRED EMBODIMENTS

It has now been found that specific food compositions (also called nutraceutical compositions) or pharmaceutical compositions can improve the functioning of living cells.

The products according the invention comprise a lipid fraction that comprises one or more of docosahexaenoic acid (DHA), docosapentaenoic acid (DPA) and eicosapentaenoic acid (EPA), and further a protein fraction, the latter providing cysteine and/or taurine equivalents and optionally a mineral fraction that comprises manganese and/or molybdenum. Optionally also a digestible carbohydrate fraction and/or a nucleotide source are beneficially included.

The lipid fraction preferably provides more than 30% of the energy that is provided by the digestible components in the formula using as calculation factors 9 kcal per g lipid, 4 kcal per gram protein or gram digestible carbohydrate and zero kcal for the other components in the product. Preferably the product comprises a lipid content of 32-80, more preferably 33-60 and still more preferably 36-50 percent of the total energy contents.

The amount of lipid fraction can be determined by applying the methods known in the art for measuring fat content in the food matrix as applicable. For example, fat content for general foods is determined by applying AOAC® official method 983.23, while the Roese-Gottlieb method (AOAC® 932.06) is better applicable for products based on dried milk (Lehner, R., Estoppey, A., (1954) *Mitt. Lebensmitteluntersuchung Hyg.* 54:183-185), and again other methods are used for measuring lipids content in infant formulae or clinical nutrition.

The amount of individual components can be determined by applying methods specifically designed for measuring that specific component or by fractionating the fat fraction isolated from the extraction of the chloroform-methanol fraction as given in the 983.23 method. When two accepted methods would differ in a statistically significant way (using P=0.05), the method, which gives the highest value is taken. The lipid fraction may include triglycerides, diacyl glycerides, monoacyl-glycerides, phospholipids, lysolecithins, glycolipids, sterols and other lipid-soluble components. For the purpose of this application the lipid fraction (and not the carbohydrate fraction) is defined to include sulfatides, cerebrosides, ceramides, sphingolipids, sphingomyelin, gangliosides and glycolipids like the globosides, hematosides and lactosylceramides. Specific analytical methods to measure the amounts of these components in a food matrix are known in the art. These amounts should therefore be added to the amounts as measured by the other methods for determining total fat, as far as they are not included in those measurements.

The polar components of the composition appear to have emulgating properties which might interfere with the emulgating systems which are conventionally used in the manufacture of homogeneous liquid formulae, which further comprise the protein, digestible carbohydrate and optionally the mineral fractions in amounts according the invention. By using milk fractions as source of these glycolipids and glycoproteins the liquid forms of the products that are suitable for complete enteral nutrition remain homogeneous.

The total lipid fraction comprises long chain polyunsaturated fatty acids (having a chain length of at least 18 and abbreviated as LCP) of the omega 3 series (ω-3), and in particular one or more of DHA, EPA and DPA. These fatty acids can be present as triglycerides, phospholipids, sphingolipids, glycolipids or other food grade forms. The amount of ω-3 LCP must be more than 400 mg per serving for adults, providing a dose of 400-3300 mg of these fatty acids per day. The concentration of the sum of DHA, EPA and DPA in the lipid fraction is 2-50, preferably 5-45, more preferably 20-40% of the lipid fraction. The concentration of the sum of EPA, DHA and DPA in a liquid product is minimally 0.2 mg to maximally 15 mg per ml, and preferably 0.3-12, more preferably 0.4-11 mg/ml. For infants the amount of w3 LCP usually should be more than 30 mg per serving, thus providing a dose of 30-1000 mg of these fatty acids per day.

In a specific embodiment, a composition of the invention comprises per 100 g:
  a) 1000 to 2000 mg of DHA+DPA+EPA;
  b) 30-80 mg cysteine+taurine
  c) 0.3-2 mg manganese+molybdene The lipid fraction comprises a relatively low amount of long chain polyunsaturated fatty acids of the omega 6 series compared to the amount of other components of the lipid fraction. The ratio ω-3/ω-6 will be in the range 0.3-5, preferably 0.4-4, more preferably 0.5-2. The amount of ω-6 LCP's will be less than 50, preferably 5-40, more preferably 8-30 wt %, most preferably 8-20 wt % and in particular 8-15 wt % of the fatty acids in the formula.

Preferably also saturated fatty acids are included. These include those fatty acids having a chain length of 8 to 24 carbon atoms. Preferably these fatty acids include those having 10, 12, 14 and 16 carbon atoms. The amount of saturated fatty acids, if present, usually should be 6-60, preferably 10-40, more preferably 12-36% by weight of the lipid phase. In particular the amount of C14:0+C16:0 usually should be 6-60, preferably 10-40, more preferably 12-36 wt % of the lipid phase. Medium chain triglycerides can origin from so called MCT oil, or origin from coconut oils or other suitable sources. The amount of MCT's usually should be 1-60, preferably 3-40 wt % of the lipid fraction. Myristic and palmitic acid can be included as acids, salts thereof, and esters with alkyl groups or acyl groups as in glycerides, or as other suitable forms. Preferably they are included as triglycerides, such as those that occur in palm kernel oil or in structured triglycerides with one additional ω-3 LCP or as diacyl or monoacyl glycerides. The monoacyl and diacyl glycerides that comprise the saturated fatty acids are preferred, because they appear to provide technological advantages, compared to the triglycerides forms, when higher amounts of lipids are included.

Oleic acid (C18:1) is preferably present in the lipid phase. It should be present in a content of 5-40 wt % of the fatty acids, preferably 6-35, more preferably 8-34 wt %. The amount in a liquid formula will be in the range of 0.1-2, preferably 0.15-1.2, more preferably 0.2-1.0 g per 100 ml liquid product.

Optionally an important part of the lipid fraction will comprise complex lipids like glycolipids, like sphingolipids such as sphingosines (e.g. sphingomyelin), acid sphingoglycolipids, such as sulfatides and gangliosides, and globosides. In the total lipid fraction the amount of material other than triglycerides and phospholipids is preferably more than 0.01 wt %, preferably 0.015-1 wt %, more preferably 0.02-0.5 wt %. The amount of sphingomyelin should be more than 130 micromolar, preferably 135-3000, more preferably 140-2000 micromolar and the amount of acid sphingoglycolipids should be more than 0.003, preferably 0.005-0.5, more preferably 0.008-0.4 wt % for best results. The amount of gangliosides should be more than 7, preferably 8-80, more preferably 9-40, in particular 9-25 mg/l liquid product. Preferred gangliosides are GD3 and GM3.

These compounds can be found in fractions that can be isolated from microorganisms like yeasts, bacteria, and in fungi, algae plants and animal material, like egg, nerve tissue, fibroblasts, and milk. It is preferred to use food grade ingredients. In particular it is preferred to use fractions from milk, such as extracts that comprise high levels of fat globules. These can be obtained from the manufacture of buttermilk and in particular in the whey that remains after manufacturing cheese from buttermilk. Suitable products that are commercially available include "buttermilk powder" and "butter serum."

Milk whey comprises a relatively high amount of small fat globules, especially when macroproteins such as β-lactoglobulin have been removed. The concentration of small fat globules can be increased by applying filtration techniques on skimmed products, which concentrate the lipid layer on one side of the membrane and remove molecules like salts and lactose. This product is called "whey microfiltrate retentate." Fractions that are enriched with acidic sphingoglycolipids can also be isolated by applying chromatographic methods known in the art such as ion exchange.

Milks from many mammals are suitable for isolation of the active components, however, milk from mares, sheep, goat and camels are particularly suited. It is most preferred to use a lipid extract isolated from sheep milk.

The amount of lipids from sheep milk should be more than 5 wt %, preferably 8-60 wt %, more preferably 10-40 wt % of the lipid fraction.

For example the fractions from egg, soy, colostrum, bone marrow, brain, milk and in particular buttermilk which are rich in fat globules, and in particular the membranes of these fat globules are of particular interest for inclusion in the products according the invention. These are concentrated in the complex glycolipids, which also comprise relatively high concentrations of carbohydrates other than glucose and fructose. Such fractions can be isolated by defattening the raw ingredients by methods known in the art, e.g. by hexane extraction or centrifugation. Additional methods should be applied to either the residual lipid—or aqueous fractions to isolate the more polar lipid fraction present as fat globule membranes. Suitable methods include selected removal of compounds of molecular weight below 300 such as minerals and lactose or removal of selected proteins, e.g. by using filtration, absorption, chromatography, osmosis techniques or precipitation.

In particular fat globules of smaller size, in particular those having a diameter less than 4.0 um, preferably less than 3.0 um, more preferably 0.001-2.0, most preferably 0.01-1.8 μm comprise the components of interest. In those situations wherein milk fat is not desired for the patient, e.g. due to a wrong fatty acid profile, it is preferred to remove at least part of the fat globules of larger size, in particular those having a diameter larger than 4.0 micrometer.

The lipid fraction from the milk should therefore preferably comprise more than 1%, more preferably 1.2-20 and most preferably 1.3-16 wt % phospholipids. In addition the lipid fraction should preferably comprise 0.1-20%, more preferably 0.2-10 and most preferably 0.6-8 wt % glycoproteins and glycolipids, and preferably 0.2-10, more preferably 0.3-9, most preferably 0.35-8 wt % cholesterol or cholesteryl esters. Preferably the lipid fraction that is isolated from milk comprises the increased amounts of at least two of phospholipids, glycoproteins, glycolipids and cholesterol and more preferably all components in amounts higher than in milk fat.

The lipid composition in the final product preferably comprises 1-80, more preferably 2-50, most preferably 3-40 wt % of the milk fraction enriched in components other than triglycerides and in particular comprising 50% more glycolipids and/or glycoproteins originating from smaller fat globule membranes of milk compared to the amount in the lipid fraction of the natural material.

Suitable methods for isolating fractions, which are enriched in fat globules, from dairy products can be found in U.S. Pat. No. 6,824,809, which is hereby incorporated by referencing. Also U.S. Pat. No. 6,391,362 discloses a suitable way to isolate a fat globule fraction from the lipid fraction of milk or cream. However, it is preferred to isolate the smaller sized fat globules therefrom, e.g. by applying micro filtration to the second aqueous phase. It is preferred not to phosphorylate the original components of the fat globule.

An additionally preferred method for isolating suitable smaller fat globules from milk is microfiltrating the aqueous phase that results after butter, cottage cheese, or quark manufacture. Especially the milk of sheep, goats and camels are suitable sources for isolating the fat globule fractions according to the invention, even though the constituents of their fat globules differ to a large extent from those in the fat globule of human milk. The fat globule fractions, which have been isolated according the methods as described, appear to be free from potentially interfering substances like prions, pathogens or viruses.

Though the fat globules or fractions thereof, that origin from the ingredients, are highly effective, they will not necessarily remain intact during the preparation or shelf life of the final product according the invention. The application of a homogenization step during processing, and the inclusion of the ingredients, which cause effectiveness of the final product, such as the protein fraction or other lipid components, interacts with the original fat globules that are present in the ingredients. Therefore typically the size of the fat globules in the product will increase and more than 50% of the lipid fraction will be provided as fat globules larger than 2 micron and in non-liposome form. More than 90% of the volume fraction of the lipids will be present in globules having a diameter larger than 0.025 um.

The lipid fraction of the final product comprises per 100 ml liquid product preferably more than 0.56 g long chain polyunsaturated fatty acids, more preferably 0.57-3.1, most preferably 0.57-2.8 and in particular 0.57-1.4 gram.

In those situations that the concentration in semi-solid and solid products is not explicitly mentioned or can not be directly derived from the claimed daily dose per daily portion, they can finally be calculated from the claimed concentrations of the active ingredients in liquid products by correcting to percentage dry mass, assuming a dry mass content of 15 g per 100 ml liquid product, 35 g per 100 g semi-solid product and 90 g mass per 100 g solid product.

In malnourished persons it is advantageous to include 0.1-10 g, preferably 0.2-5 g cholesterol sources per daily dose. Suitable sources of cholesterol include cholesterol, salts and esters thereof. Such malnourished patients may be hospital patients, patients that suffer from protein-energy malnourishment and the elderly. Not included in this group are those malnourished persons that applied bad feeding practices for longer periods, which means in particular that for several months relatively large amounts of trans fatty acids and polyunsaturated fatty acids, in particular of vegetable oils, which had become oxidized, were consumed.

The mineral fraction comprises at least manganese or molybdenum, optionally magnesium and zinc can be added. Preferably manganese and molybdenum are both included and more preferably also magnesium is included in effective amounts.

Inclusion of manganese in a diet appears important for improving membrane function of cells, in particular the membrane function of nerve cells. Especially those persons that are malnourished or have an inherited or metabolic disorder have imparted metabolic capacity for producing sphingomyelin and/or related compounds like sulfatides and glycosylated ceramides. In addition, during these disorders or during rapid growth persons experience increased needs for biosynthesis of these compounds. Examples of such persons are patients that suffer from neurological diseases, like Alzheimer's Disease, Parkinson, depression, ME, persons that suffer from systemic lupus erythamatosus (SLE), paralysis caused by nerve damage or spinal chord injury, but also young infants and fetuses, which are in a phase of growth of neural tissue, and pregnant women.

The amount of manganese administered/consumed per day should be more than 7 mg preferably 9-300 mg for a person weighing 80 kg. The concentration in a liquid product can for example be calculated by taking the daily volume and calculating the ratio of daily dose and daily volume. Assuming a volume of 2000 ml for e.g. a tube feeding gives a manganese concentration of at least 7/2000 ml=350 microgram per 100 ml. We also assume a caloric density of 1.0 kcal or 4.2 kiloJoule per ml for tube feed. The concentration per 100 kcal is therefore minimal 0.35 mg per 100 kcal, preferably 0.45-15 mg/100 kcal or >0.83, preferably 0.107-3.6 mg/100 kJ.

For infants weighing 3 kg and consuming 400 ml this minimum concentration is 0.065-mg/100 ml. For infant formulae having a energy density of 0.67 kcal/ml the concentration will therefore be more than about 0.1 mg per 100 kcal.

It was found that the inclusion of manganese as mentioned above had a promoting effect on the growth of lactobacilli in the gut, and several of the benefits associated with this effect follow from this beneficial effect, including a decrease of luminal pH, less growth of pathogens in the gut and an increase in the strength and/or capacity of the immune function, measured in terms of a decreased rate of infections and/or less diarrhea. Also a better stool consistency was observed, in particular in frequency of the occurrence of constipation. Despite increased use of manganese by these intestinal bacteria a systemic effect was observed on cell function, especially when the concentrations as given were administered.

Additional molybdenum is required to allow proper functioning of the cofactors, which appear important for creating a proper composition of the membranes, e.g. their sulfatide content, and in particular guarantees a proper functioning of nerve cells. Further, inclusion of a proper amount of molybdenum delays brain shrinkage in part of the elderly during aging. Molybdenum is also required to create a proper barrier function, e.g. of the gut, during maturation and growth or during inflammatory bowel disease and/or food allergy.

A proper amount of molybdenum means an amount of more than 2 µg per kg body weight per day, in particular 3-40, more preferably 3.6-32 µg/kgbw·d. This will typically result in a concentration of 2.0-40 ug/100 kcal [or 0.48-9.5 ug/100 kJ], preferably 2.6-30 µg/100 kcal [or 0.62-7.1 ug/100 kJ] for infant formulae, and in 15-400, preferably 18-100, more preferably 24-40 µg/100 kcal [equals respectively 3.6-95, preferably 4.3-23.8, more preferably 5.7-5.7 microgram per 100 kJ] for products for adults The amount of magnesium that is consumed per day should be 400-1000 mg, preferably 480-800 mg for a person weighing 80 kg. When a complete nutrition is designed this results in a concentration of 7.5-40 mg, preferably 9-30 mg per 100 kcal, which equals 1.8-9.5, preferably 2.1-7.1 mg/100 kJ. Magnesium appears important to allow sufficient biosynthesis of glycolipids.

Additional zinc can be included for several purposes, e.g. in order to normalize copper homeostasis. For this it should be provided in a ratio of 8-40, preferably 10-30 fold excess to copper. Normalization of copper homeostasis is important to increase the degree of saturation of ceruloplasmin with copper and to prevent excess oxidation of membrane fractions, including APP or parts thereof.

It appears important to have a balanced mineral composition. This enhances the efficacy per patient and also increases applicability in a larger group of the patients. Balance in this respect means that all of the minerals as mentioned above should be included, while also the relative amounts as indicated are important for creating a proper balance.

Suitable sources of these minerals include their salts with organic or inorganic anions like sulphate, carbonate, bicarbonate, hydroxide, chloride and citrate. Oxides of manganese and molybdenum should not be used, especially not in infant formulae. Preferably some sulphate forms are used, in such a way that sulphate provides 1-400, preferably 2-250, more preferably 3-125-mg/100 g product. Molybdenum is suitably included as molybdate salt It appeared that the effect of manganese and magnesium could be antagonized when high amounts of calcium were included in the product or when high doses of calcium were used in the total daily diet, for example when nutritional supplements were consumed next to the product according the invention. The amount of calcium to manganese in the product should therefore be 1-235:1, preferably 5-205:1, more preferably 10-100:1.

The protein fraction that is included in the product must be digestible for more than 80 wt % and preferably 90-100%. The protein fraction comprises intact proteins, peptides as may be obtained by hydrolyses of intact proteins and by syntheses, derivatives of peptides comprising more than 80% by weight amino acids, the (naturally occurring) amino acids itself, and taurine, as well as derivatives of said amino acids and taurine, like salts, N-acylated or N-acetylated forms as well as esters. Betaine, dimethylglycine, sarcosine, nucleosides material and choline also comprise nitrogen, but will not be calculated as being protein.

The protein is due to provide available cysteine and/or taurine equivalents. All proteins that typically are used in food manufacture provide cysteine. If considering dairy as a source of protein, it should be realized that casein is a relatively poor source of cysteine. It is therefore advantageous to use at least partially a whey protein, and in particular alpha-lactalbumin or whey proteins that are enriched in alpha-lactalbumin, in order to increase cysteine levels in the product. The amount of beta lactoglobulin is preferably relatively low compared to that of alpha lactalbumin in relation to the ratio as observed in natural milk.

When milk is used as protein source, it is preferred to use a protein fraction, which is also rich in proteins or peptides, which have a high degree of glycosylation, such as casein glyco macropeptide (CGMP). These proteins/peptides are defined to be those peptides in which more than 10% of the amino acid residues have been glycosylated. The amount of CGMP in the fraction of the milk that is used for inclusion in the protein fraction is preferably above 20%, more preferably more than 35, most preferably more than 40 wt %.

Preferably the protein comprises a histidine concentration of 2.5, preferably 3.0-6, more preferably 3.3-6 g per 100 g protein. This means that when whey proteins are used to a substantial degree free histidine needs to be included.

The amount of taurine should be more than 0.1 g, preferably 0.2-4, more preferably 0.4-3 g per daily dose. Typically this dose results in concentrations in liquid products of more than 5 mg, preferably 7-100, more preferably 9-60 mg per 100 g product. Also taurine salts are suitable ingredients.

Next to the above-described lipid, mineral and protein fractions, the compositions of the inventions preferably comprise other fractions, such as a carbohydrate fraction and/or a nucleotide fraction. Further, also inclusion of a vitamin fraction and/or a methyl donor fraction is preferred.

The carbohydrate fraction comprises a digestible carbohydrate fraction, which preferably includes a source of galactose and/or ribose. In order to provide sufficient energy in a carbohydrate blend that has a low glycemic index the amount of these available and digestible non-glucose sugars must be less than 50, preferably 10-40 wt % of the amount of glucose that is available to the consumer. Suitable sources of galactose or ribose are disaccharides like lactose or food grade qualities of the synthetic monosaccharides. Though the ribose from nucleotides contributes to the physiological effect of the product, it is not calculated to contribute to the total ribose content in the document, due to the relatively low doses of nucleotides in the product.

The digestible carbohydrate fraction beneficially comprises glycosamines, like mannosamine and galactosamine or N-acylated forms thereof, for example N-acetylated forms, in an amount of 0.1-10, preferably 0.2-6 wt % of the digestible carbohydrate fraction.

Part of the carbohydrates, in particular 2-50 wt % can beneficially be uronic acids as have been described in application EP 5103247.2. Part of the oligosaccharides, which have been disclosed in WO 2005/027663 is also effective for the uses as mentioned below, in particular when used with the claimed protein—and mineral fraction.

The carbohydrate fraction preferably also comprises a source of inositol. Myo-inositol is the preferred form, though up to 50% is allowed to origin from phosphorylated forms such as phytic acid equivalents such as phytases. Phosphatidylinositol also appears to be a suitable alternative.

The amount of inositol equivalents that should be administered to a person weighing 80 kg per day is 0-1500, preferably 320-1200, more preferably 380-1100 and most preferably 420-1000 mg. When calculating the desired daily dose for infants weighing 4 kg this results in 21 mg.

Other ingredients that are beneficially included in the formula include a nucleotide source. Nucleotide sources are those ingredients that after consumption result in a raise in tissue levels of xanthine, nucleotides, nucleosides and/or nucleobases in vivo. Suitable ingredients include the nucleobases like uridine, cytidine, adenine, guanidine, thymidine, their phosphorylated forms, in particular the mono-phosphorylated forms such as uridinemonophosphate, but also adenosine and guanosine, nucleosides and nucleotides.

Though beneficial effects can be observed by administering a single nucleotide source, in particular uridinemonophosphate (UMP), to the components of the claimed composition, about equally good effects, without risk of undesired side effects, can be obtained by using mixtures of nucleotides, nucleosides or nucleobases. Such mixtures are preferentially extracted from yeasts or animal tissues.

When UMP is used as source the amount per daily dose for a person weighing 80 kg must be 0.08-3 g, preferably 0.1-2, more preferably 0.15-0.9 g. The required dosages of the equivalents on weight base can be calculated from the dose of UMP by taking equimolar amounts of the nucleobases and correcting for molecular weight, using the molecular weight of UMP, which is about 324 Dalton.

Uridine derivatives like UDP, which is readily formed from dietetic UMP, appears important for transport of glycoproteins and glycolipids within the cell and availability thereof in the cytosol and plasma membrane.

The vitamin fraction, if present, should preferably comprise vitamin B6 in a food grade form, which is able to increase the levels of pyridoxal phosphate in vivo in liver and/or brain. This means that the vitamin B6 doses per day is restricted to not more than 50 mg and preferably not more than 25 mg vitamin B6 per day for a person weighing 80 kg. Effective doses are 2 mg-50 preferably 2.4-40 mg, more preferably 8-25 mg vitamin B6 for such a person. The optimal dose for a person having a different body weight can be calculated by taking the proportional part. For example for a baby weighing 3 kg the optimal dose is 37-1875 ug. Preferred forms of vitamin B6 are pyridoxamine, pyridoxal, 3-acylated pyridoxal analogues or salts thereof as disclosed in U.S. Pat. No. 6,586,414, U.S. Pat. No. 6,548,519 and U.S. Pat. No. 6,339,085, which are included by reference.

The vitamin fraction further can comprise biotin, folate and vitamin B12.

Biotin should be included in an amount of more than 1.5 μg/kgbw·d and preferably 4-50, more preferably 5-40 μg/kgbw·d. This typically results in concentrations of biotin in the product of more than 6, preferably 7-60, more preferably 8-40 μg/100 kcal for adults and >3, preferably 4-50, more preferably 4.6-30 μg/100 kcal for infants. Suitable sources of biotin are known in the art.

Folates include folic acid, folinic acid, methylated, methenylated and formylated forms of folates, their salts or esters, as well as their derivatives with one or more glutamic acid, and all in either reduced or oxidized form. Calculated to amount of folic acid the amount should be at least 300, preferably 420-2000 μg, more preferably 520-1500 μg/daily dose for an adult weighing 80 kg. For infants the recommended amount of folate per kg body weight is somewhat higher than for adults. It should be >10 μg folic acid per kgbw·d and preferably 30-140, more preferably 45-120 μg/kgbw·d.

A preferred embodiment of the formula comprises vitamin B12. In particular the vitamin B12 is not cyanocobalamine, but instead a member selected from hydroxy—or methyl cobalamins or one of the thiolatocobalamines as disclosed in WO 02/087593 or the extracts as disclosed in U.S. Pat. No. 6,187,761.

The other vitamins, such as vitamin A, D, E, K, C, B1, B2, B3 and pantothenic acid and minerals and trace elements, such as Na, K, Ca, Fe, Cu, Se, I, F comply with general recommendations for nutritional requirements, especially in infant formulae.

Additionally, a methyl donor is preferably included in the products according the invention. A methyl donor is capable of generating at least one methyl group when absorbed in the body of a mammal. Examples of suitable methyl donors include betaine, choline, serine, dimethylglycine and sarcosine. It is preferred to select betaine or dimethylglycine for effective results. The advantages of including additional methyl donors in the product become in particular apparent when the protein source comprises more than 20 wt % protein of vegetable origin, such as proteins from cereals like wheat, oats, rice, corn or soy, or seeds/tubers like peas, lupine, potato, or beans. The effective dose in such products is more than 0.18 mmol per kg body weight per daily dose, preferably 0.19-2, more preferably 0.2-1.2 millimole per kgbw·d. When, for standardization, the weight of a human body is set at 70 kg, this would mean that choline (or dimethylglycine, because having about the same molecular weight) should be present in a liquid composition with more than 1.3 g per 2 liter product. A liquid supplement for use by an adult consumer in an amount of 400 ml per day would comprise 1.3 g per 400 ml.

The choline resulting from phospholipids is not calculated to contribute to this amount of methyl donor.

The fortification with one or more methyl donors is especially advantageous if the amount of methyl acceptor remains low in the product in comparison with the amount of methyl donor. In particular it is advantageous to have more than 3 fold molar excess of methyl donors compared to the molar amount of methyl acceptors, such as glycine, phosphatidylethanolamine and polyamines such as spermine and spermidine.

Furthermore, statins can be beneficially included in those products that are used by patients suffering from dyslipidemias and in particular hypercholesterolaemia. Admixture would be useful for periods shorter than 2 weeks in those cases that a rapid decrease of plasma cholesterol levels is envisaged. The compounds may increase the efficacy of the compositions of the invention during this period. However, a disadvantage on the longer term of including compounds like simvastatin, lovastatin, rosuvastatin, pravastatin, fluvastatin and atorvastatin is their capability to inhibit potently the action of hydroxymethyl glutaryl-CoA reductase when administered in relatively small amounts. Therefore, if the product is consumed for longer periods in conjunction with statins, the product should comprise one or more of the group of ubiquinons, ubiquinols, menaquinons, coenzyme Q10, dolichol, dolichol esters, dolichol ethers, synthetic poly-isoprenoids having more than 8 isoprenoid units, such isoprenoids with one or more a carboxylic acid groups, hydroxy groups having retinoids, lycopene, and sterols in amounts to counteract the disadvantages of administering statins. Preferably dolichol or its analogues are included, wherein the dolichol analogues are substantially apolar for at least 80% of the molecule. Maximally fifteen percent, but preferably less than 10% of the carbon atoms is allowed to be substituted with polar groups such as hydroxy, alkoxy in particular methoxy, carboxyl, sulfhydryl, substituted sulfhydryl, amino, substituted amino, alkyl or acyl moieties.

These inclusions are required to maintain efficacy of the product as an improver of immune function e.g. in cancer patients, and in particular as a product that decreases sensitivity to metastasis formation. In combination with statin therapy the products even appear advantageous if used without the protein and mineral fraction of the product in claim 1 under the condition that the above-mentioned components are included in an amount of at least 20 mg dolichol analogues, at least 4 mg retinoids, at least 4 mg ubiquinons, ubiquinols, menaquinols or menaquinons, and at least 0.02 mg sterols per daily dose. Suitable sterols are in particular natural sterols as occur in mammalian organisms.

Effects

The products according to the invention normalize membrane function of nerve cells, especially when these membranes are deformed and/or have a wrong composition. Though one may speculate about the cause of these defects, it seems that a dysfunction of one or more membrane-bound enzymes, e.g. an upregulation of sphingomyelinase, which decreases sphingomyelin content and increases ceramides levels, seems to be important to this pathology. Also exposure to high amounts of stressors, a genetic disposition and/or chronic malnourishment may contribute to more rapid development of imparted nerve functioning.

Persons older than 50 years of age are particularly prone to developing such condition, by a combination of aging and non-optimal nourishment. Prevalence of high amounts of nerve cells having deformed membranes will result in e.g. impairment of cognitive function, sensory awareness and insufficient capability to control the motoric system (muscles). Nerve cells that possess deformed membranes will start to synthesize increased amounts of Aβ (Abeta) proteins, which induce amyloid deposits, forming plaques and/or neurofibrillary tangles. The deformed membrane will also start to become a host for several lipophilic compounds like several peptides that are soluble in this matrix such as the dimers of Aβ, in particular of Aβ 42, which may result in release of apoptosis signals and death of nerve cells.

In the end this may lead to shrinkage of the brain volume and in particular of the volume of the white matter, especially in the very old. Syndromes caused by these effects are generally known as dementia or Alzheimer's disease, although specific forms of these diseases have been described.

Neuropathy is partially caused under conditions wherein an organism and in particular the neural tissue is exposed for a longer period of time to increased levels of reducing equivalents, in particular of hydrogenated nicotinamide dinucleotide (NADH). Such levels are increased in e.g. persons suffering from insulin resistance, like diabetics, persons that suffer from ischaemia (e.g. after surgery or after been subjected to other physiological trauma which imparts blood flow to tissues) or persons that abuse ethanol.

One may discriminate between neuropathies that occur centrally (brain and spinal chord) and peripheral neuropathies. The compositions according to the invention are effective in both types. Central insulin resistance may result in pathologies as Alzheimer's or Parkinson's diseases. Peripheral neuropathy may impart motoric and sensoric functions and/or result in pains as explained below. Such neuropathies may also include neural function in specific organs like the liver. Without wanting to be bound by theory it may be important that the compositions according the invention decrease cytosolic sialidase activity and increase the rate of biosynthesis of essential constituents of nerve cells including sulfatides and gangliosides.

Neuropathy as caused by antibody attack also appears to be decreased. Without wanting to be bound by theory it seems important that the improvement of the function of Schwann-type cells, in particular in terms of repairing damaged myelin and cellular debris, contributes to this effect, as does the improvement of the integrity of blood-nerve barrier and decrease of the activation state of glial cells in the spinal chord in such types of diseased persons. This makes the compositions of the invention useful in the treatment of multiple sclerosis and in the decrease of chronic or neuropathic pain (contrary to normal pain).

Administration of the compositions according the invention appeared to improve interaction between nerve cells, which effect had major consequences for many reactions of the body to outside triggers. For example proper notification and handling of sensory triggers and adequate definition of motoric functions as a reaction to these triggers was improved. Interaction is essential to the thought process and awareness of emotions, including feelings of fear and pain (including threshold function).

In addition proper functioning of many organs and/or cells, that are at least partially controlled by the nervus vagus or that react to local acetylcholine release e.g. by epithelial cells and macrophages, depends on the capability of nerve cells to handle these signals properly. Examples of such reactions include the activity of the gastrointestinal tract after sensory awareness of meal components, and the activity of the heart in rest (arrhythmias) and during exercise. Another example is the activity of the immune system, in particular the immune cells that circulate in blood, in lymph and in particular in the epithelial cells of lung and the gastrointestinal tract. These cells include the activity of cells that produce mucus (Goblet cells) and the glycocalyx, the antigen presenting cells, Paneth cells and Peyer's patches, and lymphocytes as locally present in the lamina propria, which are all strongly influenced by their membrane composition and function.

The improvement of the functioning of the central nervous system, including the autonomous nerve system and the hypothalamus, includes the functioning of the white matter, and results in better thinking capabilities, enhanced emotional feelings, communication skills and memory function.

It is claimed by the inventors that apart from neurotransmitter release and receptor function (notably G-protein receptors) also the composition of the membranes of nerve cells is improved, and in particular their content of polar lipid-like components like sulfatides, ceramides, sphingolipids, glycoproteins and glycolipids in relation to the total mass of the membrane and/or in relation to the amount of non-polar components. Examples of non-polar compounds are cholesterol and dimeric peptides, in particular the amount of homo-dimeric non-polar peptides of larger membrane proteins like the amyloid precursor protein, more in particular the dimeric form of the Aβ-42 fragment. In this way it is aimed to change size and composition of membrane rafts and to maintain a proper functioning of the active parts of the rafts. In this way not only the function of the receptor changes (which may be due to a modification of the affinity of ligand molecules for the receptors and an increase of discriminatory power, or a change in intrinsic activity of the ligands e.g. by influencing secondary messages such as the IP3 pathway); also the activity of glycoproteins and membrane-bound enzymes changes. In this way significant changes in metabolic and physiological activities of living cells are achieved. This applies in particular to the functioning of nerve cells, immune cells, bone marrow cells, stem cells and blood cells like erythrocytes. It was found by the inventors that acetylcholine biosynthesis and transport are improved by administering the composition according the invention. The function of membrane-bound choline acetyltransferase (ChAT) was improved as well as its transport over the vesicle membrane into the synaptic cleft. Acetylcholine release is an essential part of brain function, which includes cognitive function and also of the activity of the parasympathetic nerve system, in particular the nervus vagus. This part of the nervous system regulates gastrointestinal behavior and for example heart rhythm. Improvement of heart arrhythmias, gut motility and gut-mediated systemic immune reaction is obtained by administering the composition according to the invention.

The compositions according the invention are also useful in repair of damaged nerve tissue. Nerve lesions can occur after trauma, for example surgery or spinal chord injury, but also in brain after chronic exposure to high diastolic blood pressure.

The compositions according to the invention are also useful in the treatment of multiple sclerosis. The demyelination process is slowed down as well as the creation of demyelinated plaques in the brain.

In patients suffering from Parkinson's disease, in particular idiopathic Parkinson's disease (PD), the compositions according to the invention decrease the rate of deterioration of the substantia nigra cells. In particular the amount of amyloid plaques as well as the amount of alpha-synuclein and Lewy bodies in brain will decrease in PD patients, but also in patients suffering from specific forms of dementias, e.g. Lewy body dementia, or suffering from multiple system atrophy (MSA) and amyotrophic lateral sclerosis (ALS).

Such precipitation of excess amounts of proteins in the brain, in particular in neurons and glial cells, such as the occurrence of polyglutamate expansions during Huntington's disease, and tau-protein in various forms of dementia, palsy and corticobasal degeneration, can be conveniently counteracted by intervention with the compositions according the invention. Change of the intracellular membranes, e.g. those of the Golgi apparatus and/or endoplasmatic reticulum, and a consequent different modification of the proteins may also play a role in establishing this effect.

When used in administration to patients suffering from insulin resistance, and to babies or infants it is important to include components, which increase insulin sensitivity, such as a protein fraction comprising all essential amino acids and having a relatively high aspartate to glutamate ratio, in particular above 0.42, preferably 0.44-0.8, more preferably 0.45-0.6 or a vitamin fraction, which comprises at least riboflavin equivalents, vitamin B6 and/or biotin or preferably all three vitamins. Examples of such protein fractions include alpha-lactalbumin or protein blends to which aspartic acid has been added.

In case the composition is administered to subjects suffering from diabetes, it is further beneficial to administer the composition as adjuvant to metformin and to refrain from co-administration with drugs, which are known to decrease insulin sensitivity. For subjects that suffer from insulin resistance it is further preferred to include a fiber or fiber-like material that comprises resistant starch for more than 20 wt % of the fiber blend in the composition. Also for diabetics and obese subjects inclusion of a fiber-like material, such as slowly digestible starch, galacto oligosaccharides, cellulose or fructo oligofructose/oligofructose, is advantageous. for these groups a content of about 30 wt % or more starch is advisable.

The active components in the compositions according to the invention further regulate maturation of the eye and brain during fetal development. The compositions according the invention are therefore useful for administration to pregnant women, for allowing the development of good visual and brain functions in babies, including cognitive and mental capabilities.

Improved communication between nervous cells appears to be important in combating epileptic convulsions, and reducing the frequency and intensity of schizophrenia, in decreasing the rate of attacks in subjects suffering from Gilles de la Tourette syndrome, in reducing ADHD and autistic behavior and in improving sleep behavior.

For combating acute situations in these disorders, the compositions according to the invention should be included in a ketogenic diet. In particular the caloric value of the nutritional product according the invention must be more than 40% of the caloric value of the protein, lipid and digestible carbohydrate fraction in the product. Preferably this amount is more than 46, more preferably more than 50%. In such ketogenic products the lipid fraction must meet the criteria as mentioned above. The amount of ω-6 long chain polyunsaturated fatty acids should be relatively low and the amount of saturated fatty acids relatively high.

The active components as present in the compositions according to the invention also appear to be essential for proper maturation of the gut and proper development of its barrier, immune and transport function. This effect becomes evident from the reduced sensitivity to intestinal infections, a reduced rate of diarrhea and bacterial overgrowth, and less sensitivity to food-born allergens of subjects that have obtained such condition of the gut.

Without wanting to be bound by theory it is thought that it is important that the products according to the invention improve membrane function of epithelial cells, of receptors like the CD1d receptor and that they increase the proper action of dendritic cells. This proper action includes the release of chemokines and cytokines, which recruit the right type of lymphocytes, provide a proper "Th1/Th2" response and direct a proper migration of these cells to the lymph nodes. These effects decrease the rate of pathogen translocation and pathogen recognition. It is thought that the recruitment of the right types of T-cells helps to combat undesired cells like allergens, pathogens and mutated cells and defines a proper response, e.g. an allergic reaction for the organism. Due to the modified composition of the plasma membrane of e.g. endothelial cells, pathogens and/or allergens, in particular allergens that comprise a hydrophobic part, adhere less and/or differently, which causes a more appropriate reaction. In addition the composition of mucin produced by epithelial cells will improve, in particular with regard to the amount of sulfated and sialylated components.

For obtaining maximal improvement of the condition of the gut, particularly in malnourished patients, the compositions according to the invention should comprise a source of cholesterol. In particular the amount must be in the range of 2-100, preferably 6-60, most preferably 9-40 mg per 100 g. Suitable sources are free cholesterol or cholesteryl esters, in particular with oleic acid, or a mixture thereof, preferably in a ratio of free to esterified cholesterol from 4-10:1.

It is also thought that the above mentioned effects with respect to the immune system can also be held responsible for the improvement in response to a proinflammatory trigger and the decrease in magnitude of an autoimmune reaction. This appears applicable in the treatment of chronic inflammatory diseases, in particular arthritis, hepatitis, pancreatitis and chronic bronchitis and in the treatment of young infants susceptible to developing diabetes type I and older adults which appear to develop rheumatoid diseases, like rheumatoid arthritis and multiple sclerosis.

The compositions according the invention facilitate lung development and proper repair of lung tissue, e.g. after burns, exposure to toxicants, emphysema, and chronic physical exposure like chronic coughing and during inflammation and related lung infections and as results from pulmonary obstructive diseases like COPD and bronchitis.

Lung tissue comprises large amounts of specific surfactant molecules, whose rate of biosynthesis is increased by the compositions according to the invention. The compositions are particularly useful for pregnant women for improving fetal lung development, for infants having small gestational age, and in particular those that are sensitive to the respiratory distress syndrome. Problems with lung development can be identified by analyzing at a proper moment, e.g. after 6 months gestation, the composition of the amniotic fluid and in particular the amount of sphingomyelin in relation to that of other lipid components.

When provided to patients for improving lung function the lipid fraction should comprise a relatively high amount of palmitic acid (C16:0), in particular more than 10 wt % of the fatty acids of the total lipid fraction, and more in particular 10.5-18-wt %. Palmitic acid should preferably have for more than 15% the sn2 position in the triglycerides fraction.

Efficacy of the formulations according to the invention in the treatment of COPD can be established by measuring parameters indicative of respiratory capacity, e.g. FEV 1.0, and/or measuring the expression of different types of muscarinic receptors and chemokines secretion by sputum cells, like disclosed in Profita M., et al. (*Allergy*, 2005, 60:1361-1369)

The compositions according the invention improve recognition of undesired cells in the body such as mutated or tumor cells and change the pattern of cytokine production by macrophages that were stimulated by antigens. They therefore reduce the risk of developing tumors and decrease the rate of recurrence of tumors after resection or destruction by other means, such as radio- or chemotherapy, and decrease the rate of metastasis formation.

The composition and constitution of the cell membranes appears to influence transport of reducing equivalents within the cell, for example in the development of sensitivity to insulin. The compositions according the invention therefore diminish the tendency to develop obesity during childhood but also during adult life.

In combating obesity, the compositions appear to decrease the amount of circulating C reactive protein (CRP) and to decrease the release of CRP by the adipose tissue. Endogenous synthesis of resistin by adipose tissue is increased. In this way the incidence of cardiovascular disease in persons suffering from the metabolic syndrome, and in particular the development of arteriosclerosis and high blood pressure in obese persons, is decreased.

Endocrine function of specific organs and organelles, which include the function of pancreas, hypothalamus and the Golgi and ER organelles in liver and vesicle biosynthesis in and release of endocrine messengers from nerve cells, is improved. The compositions according to the invention are claimed to support release of insulin by the pancreas, secretion of digestive enzymes in cystic fibrosis patients, appropriate reaction of hypophyse to signals that arrive at or are produced by other parts of the body, and immune function, especially the clearing function of Kupffer cells as well as the biosynthetic role of organs that produce acute phase proteins.

The compositions can be beneficially used in combination with several types of drugs for the purposes as mentioned above. The use of the product in combination with large planar molecules like statins has been discussed above, in particular in relation to the treatment of cognitive impairment in the elderly, which suffer from dyslipidaemia. Typically a relatively large part of these patients have a relatively high amount of plaques and tangles.

The compositions of the invention can also be advantageously used in combination with phosphodiesterase inhibitors, when aiming improvement of cognitive function, in particular when the drugs are used for periods shorter than about one month and when the dose of the inhibitors in this period is less than 10 mg, preferably less than 2 mg per day for an adult.

The products according the invention are also advantageously used in combination with, or as adjuvant to vaccine therapy of amyloid formation. The rapid decrease in the amount of amyloid in brain is supported by biosynthesis of better membranes which thus prevents the deleterious effects of residual excess amyloid.

Typically it requires at least several days before the effectivity of the compositions manifests itself. Optimal results are obtained by applying administration regimens in humans, which achieve a daily use of the product for longer than 1 week, in particular longer than 2 weeks. The administration protocol may include a loading phase wherein during the first week 2 or 3 daily dosages are administered. Thereafter the daily dosages which have been disclosed in this document have to be applied for optimal results.

EXAMPLES

Example 1

Introduction

In Alzheimer patients one of the hallmarks is the presence of beta-amyloid (Aβ) plaques. Formation of Aβ plaques causes a reduction in production capacity of acetylcholine, a neurotransmitter involved in learning and memory processes. The reduction in acetylcholine levels results in memory loss [Isacson, 2002 #766]. Injecting rats with a solution containing Aβ results in similar problems in learning and memory [Nakamura, 2001 #621]. This model is well accepted to test the effects of beneficial compounds on Aβ-induced memory loss. This experiment is addressing the effects of Aβ infusion on acetylcholine producing cells and the transporter for acetylcholine. Furthermore, a dietary composition is used to prevent these effects.

Experimental Design

Four groups of rats received either an infusion into the lateral ventricle with beta-amyloid or a saline solution. Five weeks prior to the infusions the rats were fed one of two diets, A or B. The four groups are summarized in table 1. Table lists the dietary composition of the two diets. Diet A serves as a control diet. Diet B is enriched in DHA, EPA and phospholipids to improve membrane quality. Furthermore, it is enriched in UMP and choline to stimulate membrane synthesis. And it is enriched in B-vitamins and folic acid to relieve homocysteine levels.

TABLE 1

Groups of Rats Differing in Infusion Solutions and Diet

| Group | Infusion | Diet |
|---|---|---|
| 1 (sham) | Saline | A |
| 2 | Abeta | A |
| 3 (sham) | Saline | B |
| 4 | Abeta | B |

TABLE 2

Composition of the Diets

| | | Diet A | Diet B |
|---|---|---|---|
| | | g/100 g fat | g/100 g fat |
| Fatty acids | LA | 31.1 | 30.0 |
| | ALA | 1.3 | 2.9 |
| | EPA | 0.0 | 0.0 |
| | DHA | — | 3.3 |
| | total ω-6 | 31.1 | 30.4 |
| | total ω-3 | 1.3 | 13.0 |
| | ω-6/ω-3 | 23.5 | 2.3 |
| | | mg/100 g food | mg/100 g food |
| Phospholipids | Soya Lecithin | — | 500 |
| | PC | — | 130 |
| | PS | — | 20 |
| | | g/100 g food | g/100 g food |
| | Choline | — | 0.95 |
| | UMP | — | 1.55 |
| | | mg/100 g food | mg/100 g food |
| vitamins | A | 400 | 400 |
| | D3 | 100 | 100 |
| | E | 3 | 253 |
| | K3 | 0.005 | 0.005 |
| | B1 | 0.4 | 0.4 |
| | B2 | 0.3 | 0.3 |
| | B6 | 0.6 | 4.725 |
| | B12 | 0.005 | 0.00575 |
| | Vitamin C | 0 | 200 |
| | Niacin | 2 | 2 |
| | Pantothenic acid | 0.8 | 0.8 |
| | Choline | 86.8 | 86.8 |
| | Folic acid | 0.1 | 1.35 |
| | Biotin | 0.2 | 0.2 |
| minerals | Iron | 3.5 | 3.5 |
| | Copper | 0.4 | 0.4 |
| | Zinc | 1.2 | 1.2 |
| | Manganese | 5 | 5 |
| | Iodide | 0.015 | 0.015 |
| | Selenium | 0.009 | 0.159 |
| | Cobalt | 0 | 0 |
| | Chromium | 0.029 | 0.029 |
| | Nickel | 0.007 | 0.007 |
| | Fluor | 0.09 | 0.09 |
| | Tin | 0.1 | 0.1 |
| | Vanadium | 0.009 | 0.009 |

Results

Table 3 (and FIG. 1) lists the effects of Aβ infusion and dietary intervention on production and transport potential of acetylcholine. Aβ infusions in diet A fed rats resulted in a reduction of acetylcholine producing cells (ChAT) and in transport capabilities for acetylcholine (VAChT). Feeding diet B completely restored production and transport capacity of acetylcholine to normal levels.

TABLE 3

Results of ChAT and VAChT

| | Diet A | | Diet B | |
|---|---|---|---|---|
| | Sham | Abeta | Sham | Abeta |
| ChAT | 407.3 ± 29.27 | 309.4 ± 96.76 | 395.6 ± 62.6 | 404.0 ± 102.0 |
| VAChT | 296.3 ± 38.4 | 228.9 ± 53.31 | 271.4 ± 65.3 | 274.8 ± 58.8 |

Discussion and Conclusion

Lateral ventricle infusions of Aβ induce a reduction in acetylcholine production and in transport capacity of acetylcholine. These effects were completely diminished by feeding a diet enriched in omega-3 fatty acids, phospholipids, B-vitamins and UMP/choline.

Example 2

Ready-to-Use Liquid Product for Improving Cognitive Function in Persons Above 50 Years of Age Providing Per 100 ml Energy 50-120 kcal; Protein 1-10 g; lipids 1-5 g; digestible carbohydrates 4-20 g, and which comprises:

| | |
|---|---|
| a- | DHA + DPA + EPA = 1000-2000 mg |
| b- | 30-280 mg cysteine or taurine |
| c- | 100-1000 mg phospholipids |
| d- | 0.5-3 mg vitamin B6 |
| e- | 50-500 ug folic acid |
| f- | 1-30 ug vitamin B12 |
| g- | 0.07-2 mg Manganese |
| h- | 0.07-2 mg molybdenum |

Example 3

Ready-to-Drink Liquid for Alzheimer Patients that Comprises Per 100 ml

| | |
|---|---|
| Energy | 100 kcal |
| Protein | 3.06 g (casein, whey 80/20) |
| Carbohydrates | 13.3 g (maltodextrins, sucrose) |
| Fat | 3.73 g (fish oil, phospholipids) |
| Comprising 0.96 g DHA and 0.24 g EPA | |
| Uridine monophosphate | 0.5 g (disodium salt) |
| Choline | 0.32 g |
| Vitamin E | 32 mg alpha-tocopherol |
| Vitamin C | 64 mg |
| Selenium | 48 µg |
| Vitamin B6 | 0.8 mg |
| Folic acid | 0.32 mg |
| Vitamin B12 | 2.4 µg |
| Magnesium | 20 mg |
| Zinc | 1.2 mg |
| Manganese | 0.3 mg |
| Molybdenum | 10 µg |

Also 0.12 g NA, 0.15 g K, 0.12 g Cl, 80 mg Ca, 70 mg P, 1.6 mg Fe, 13.3 µg I, 0.18 mg Cu, 6.7 µg Cr, 0.1 mg F, 0.16 mg vit A, 0.15 mg B1, 0.16 mg B2, 1.8 mg B3, 0.53 mg B5, 0.7 µg D, 4.0 µg biotin and 5.3 µg vitamin K are included.

Example 4

Powdered Anti-Allergic Infant Formulae, which Provide after Fresh Reconstitution of 15.4 g Powder Per 100 ml Water

| | | |
|---|---|---|
| Energy | 64-80 kcal | |
| Protein fraction | 1.0-2.0 g | based exclusively on free amino acids or their salts, and which comprises at least 2 wt % cysteine and 0.2 wt % taurine |
| Lipids | 2-4 g | which provides 2 wt % DHA based on the total sum of fatty acids ingredients include 5-40 wt % buttermilk fat and 0.5-8 wt % egg lipids including lecithin |
| Nucleotide equiv. | 1-40 mg | Mixture of UMP and yeast extract |
| Manganese | 65-1000 µg | included as salt, in particular $MnSO_4$ |
| Molybdenum | 2.3-300 ug | included as salt, in particular molybdate salt |
| Choline equiv. | 20-200 mg | included as choline salt, in particular choline bitartrate |

In this example the determination of the amount of the additional components that are included, such as Na, K, Cl, Ca, P, Fe, Cu, Zn, Se, Cr, I, vit A, D, E, K, B1, B2, B3, B5, B6, B12, B11, biotine and C follows recommendations for infant formulae. Also myo-inositol was included.

Example 5

Product for Patients that Suffer from Depressed Immune Function

Liquid Ready-to-Use Product that Comprises Per 100 ml:

| | |
|---|---|
| Energy | 630 kJ (or 110 kcal) |
| Protein | 4.0 g (buttermilk whey/casein 20-80) |
| Carbohydrates | 12.4 (3 g lactose, maltodextrins, slowly digestible starch) |
| Lipids | 5.3 (1 g milk fat, 1 g marine oil, 0.6 g egg lipids, 2.7 g vegetable oil) |
| Manganese | 1 mg |
| Molybdenum | 0.1 mg |
| Betaine | 100 mg |
| Fibre | 1.0 g (resistant starch, galactooligosaccharides 50/50) |

Na 0.1 g, K 0.2 g, Cl 0.13 g, Ca 0.8, P 0.8, Mg 50 mg, Fe 2.4 mg, Zn 2.4 mg, Cu 0.3 mg, F 0.15, Se 8.6 ug, Cr 10 ug, I 20 ug, vit A 0.12 mg RE, D 1.1 ug, E1.6 mg TE, K 8 ug, B1 0.23 mg, B2 0.24 mg, B3 2.7 mg NE, Pantothenic acid 1.0 mg, B6 0.8 mg, B11 80 ug, B12 0.4 ug, biotin 10 ug, C 12 mg

Example 6

Product for Patients Suffering from Cancer, HIV, Bone Marrow Transplantation, Heart Failure or COPD Liquid Ready-to-Use Composition Based on Full Fat Pasteurized Milk from Sheep or Camels, which Comprises Per 100 ml:

0.4 g algae oil, 0.4 g Betaine, 0.4 g ribose, and 0.2 g histidine and further Na 50 mg, K 160 mg, Cl 100, Ca 150 mg, P 120 mg, Mg 52 mg, Fe 3 mg, Zn 2.8 mg, Cu 0.4 mg, Mn 3 mg, F 0.2 mg, Mo 200 ug, Se 11 ug, Cr 13 ug, I 25 µg, vitamin A 188 µg RE, D1.3 µg, E 2.3 mg a-TE, K 10 µg, B1 0.3 mg, B2 0.3 mg, B3 3.4 mg NE, pantothenic acid 2 mg, B6 (as pyridoxal) 0.6 mg, folic acid 100 µg, B12 0.7 µg, biotin 7.5 µg, and dimethylglycine 80 mg.

Example 7

Product for Preventing Obesity

Liquid Product that Comprises Per 100 ml:

| | |
|---|---|
| Energy | 336 kJ |
| Protein | 4.0 g (3.6 g soy protein isolate, 0.2 g aspartate, 0.2 g histidine) |
| Lipids | 4.0 g (dolichol 0.2 g, phospholipids 1 g, milk globule membrane enriched fat fraction 0.6 g, marine oil 1.0 g, rapeseed oil 0.5 g, sunflower 0.7 g, corn oil 0.5 g) |
| Carbohydrates | 12 g (lactose 2 g, maltodextrins 6 g, slowly digestible starch 2 g, 2 g sucrose) |
| Manganese | 1 mg |
| Molydenum | 0.1 mg |
| Betaine | 100 mg |
| Fibre | 1.0 g (resistant starch, galacto-oligosaccharides 50/50) |

Na 0.1 g, K 0.2 g, Cl 0.13 g, Ca 0.8, P 0.8, Mg 50 mg, Fe 2.4 mg, Zn 2.4 mg, Cu 0.3 mg, F 0.15, Se 8.6 µg, Cr 10 µg, I 20 µg, vit A 0.12 mg Re, D1.1 µg, E1.6 mg TE, K 8 µg, B1 0.23 mg, B2 0.24 mg, B3 2.7 mg NE, Pantothenic acid 1.0 mg, B6 0.8 mg, B11 80 µg, B12 0.4 µg, biotin 10 µg, C 12 mg

Example 8

Liquid Ready-to-Use Product for Diabetic Patient Suffering from Neuropathy that Comprises Per 100 ml

| | |
|---|---|
| Protein | 4.75 g (Pea protein, buttermilk whey) |
| Lipids | 3.78 g (fat fraction from sheep milk comprising 20% fat globules from small size 0.4 g, egg lipids 1 g, vegetable oils 1.98 g and 0.4 g marine oils) |
| Carbohydrates | 11.75 g |
| Galactose | 1.5 |
| Palatinose | 3.0 |
| Slowly digestible starch | 1.0 |
| Fructose | 0.2 |
| Maltodextrins | 3 |
| Glucose | 2 |
| Isomalto oligosaccharides | 1.05 |
| Fibres | 2.0 g |
| Galacto oligosaccharides | 1.0 |
| Resistant starch | 0.6 |
| Cellulose | 0.1 |
| Fructo oligofructose/oligofructose | 0.3 g |
| Baker's yeast | 0.3 g |

Vitamins, Minerals According to Example 2

Example 9

Product for Pregnant Women

| | |
|---|---|
| Protein | 3.06 g (casein, whey 80/20) |
| Carbohydrates | 13.3 g (maltodextrins, sucrose) |
| Fat | 3.73 g (fish oil, glycolipids rich fraction from sheep milk) comprising 0.96 g DHA and 0.24 g EPA |
| Uridine monophosphate | 0.5 g (disodium salt) |
| Dimethyl glycine | 0.6 g |
| Vitamin E | 12 mg alpha-tocopherol |
| Vitamin C | 24 mg |
| Selenium | 38 µg |
| Vitamin B6 | 0.8 mg |
| Folic acid | 0.32 mg |
| Vitamin B12 | 4.4 µg |
| Magnesium | 30 mg |
| Zinc | 1.5 mg |
| Manganese | 0.3 mg |
| Molybdenum | 20 µg |

Also 0.12 g NA, 0.15 g K, 0.12 g Cl, 80 mg Ca, 70 mg P, 1.6 mg Fe, 13.3 µg I, 0.18 mg Cu, 6.7 µg Cr, 0.1 mg F, 0.16 mg vit A, 0.15 mg B1, 0.16 mg B2, 1.8 mg B3, 0.53 mg B5, 0.7 µg D, 4.0 µg biotin and 5.3 µg vitamin K are included.

The invention claimed is:

1. A composition comprising a lipid fraction having at least one of docosahexaenoic acid (DHA), docosapentaenoic acid (DPA) and eicosapentaenoic acid (EPA), a nucleotide fraction, a protein fraction including cysteine, a phospholipid, a vitamin, and a mineral fraction including manganese or molybdenum, wherein the lipid fraction comprises an ω-6 polyunsaturated fatty acid having 18 or more carbon atoms in an amount of 8-30 wt % of the fatty acids.

2. A composition comprising a lipid fraction having at least one of docosahexaenoic acid (DHA), docosapentaenoic acid (DPA) and eicosapentaenoic acid (EPA), a nucleotide fraction, a protein fraction including cysteine, a phospholipid, a vitamin, and a mineral fraction including manganese or molybdenum, wherein the lipid fraction comprises more than 0.01 wt % of at least one of glycolipids, gangliosides, sulfatides or sphingomyelin.

3. The composition according to claim 1, wherein the nucleotide fraction includes nucleotides or nucleosides.

4. The composition according to claim 1, further comprising a digestible carbohydrate fraction providing a source of galactose or ribose.

5. The composition according to claim 1, wherein the lipid fraction includes a lipid from a dairy product, from eggs or from the endosperm of plant seeds or beans.

6. The composition according to claim 1, wherein the lipid fraction comprises fat globules having a size of 0.001-10 µm.

7. A composition comprising a lipid fraction having at least one of docosahexaenoic acid (DHA), docosapentaenoic acid (DPA) and eicosapentaenoic acid (EPA), a nucleotide fraction, a protein fraction including cysteine, a phospholipid, a vitamin, and a mineral fraction including manganese or molybdenum, wherein the lipid comprises 1.3-16 wt % phospholipids or 0.1-20 wt % glycoproteins and glycolipids.

8. A composition comprising a lipid fraction having at least one of docosahexaenoic acid (DHA), docosapentaenoic acid (DPA) and eicosapentaenoic acid (EPA), a nucleotide fraction, a protein fraction including cysteine, a phospholipid, a vitamin, and a mineral fraction including manganese or molybdenum, wherein the protein fraction has a weight ratio of aspartate to glutamate of at least 0.42.

9. A composition comprising a lipid fraction having at least one of docosahexaenoic acid (DHA), docosapentaenoic acid (DPA) and eicosapentaenoic acid (EPA), a nucleotide fraction, a protein fraction including cysteine, a phospholipid, a vitamin, and a mineral fraction including manganese or molybdenum, having an energy content of 50-120 kcal, a protein content of 1-10 g, a lipids content of lipids 1-5 g, and a content of digestible carbohydrates of 4-20 g, and further comprising:
  a) at least one of DHA, DPA or EPA in a sum amount of 400-3300 mg
  b) 30-280 mg cysteine
  c) 100-1000 mg phospholipids
  d) 0.5-3 mg vitamin B6
  e) 50-500 ug folic acid
  f) 1-30 ug vitamin B12, and
  g) 0.07-2 mg manganese.

10. The composition according to claim 1 wherein the nucleotide is a monophosphate.

11. The composition according to claim 1 wherein the nucleotide is uridine monophosphate.

12. The composition according to claim 3 wherein the nucleoside is adenosine or guanosine.

13. The composition according to claim 2 wherein the nucleotide is a monophosphate.

14. The composition according to claim 2 wherein the nucleotide is uridine monophosphate.

15. The composition according to claim 7 wherein the nucleotide is a monophosphate.

16. The composition according to claim 7 wherein the nucleotide is uridine monophosphate.

17. The composition according to claim 8 wherein the nucleotide is a monophosphate.

18. The composition according to claim 8 wherein the nucleotide is uridine monophosphate.

19. The composition according to claim 9 wherein the nucleotide is a monophosphate.

20. The composition according to claim 9 wherein the nucleotide is uridine monophosphate.

* * * * *